(12) United States Patent
Lin et al.

(10) Patent No.: US 7,026,009 B2
(45) Date of Patent: Apr. 11, 2006

(54) EVALUATION OF CHAMBER COMPONENTS HAVING TEXTURED COATINGS

(75) Inventors: Shyh-Nung Lin, Los Gatos, CA (US); Mark D. Menzie, Sunnyvale, CA (US); Nimoal Sun, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 256 days.

(21) Appl. No.: 10/113,847

(22) Filed: Mar. 27, 2002

(65) Prior Publication Data

US 2003/0185965 A1 Oct. 2, 2003

(51) Int. Cl.
*B05D 1/02* (2006.01)
*B05D 1/08* (2006.01)
*C23C 4/08* (2006.01)
*C23C 4/10* (2006.01)

(52) U.S. Cl. ............... 427/8; 427/450; 427/452; 427/453; 427/456; 219/121.47; 118/723 R; 117/85

(58) Field of Classification Search ............... 427/8, 427/446, 450, 452, 453, 456; 117/85, 86, 117/92, 103; 219/121.47; 118/722, 723, 118/728; 216/63–71
See application file for complete search history.

(56) References Cited

U.S. PATENT DOCUMENTS

| | | | |
|---|---|---|---|
| 4,491,496 A | 1/1985 | Laporte et al. | |
| 4,717,462 A | 1/1988 | Homma et al. | |
| 5,032,469 A * | 7/1991 | Merz et al. | |
| 5,391,275 A | 2/1995 | Mintz | |
| 5,401,319 A | 3/1995 | Banholzer et al. | |
| 5,474,649 A | 12/1995 | Kava et al. | |
| 5,509,558 A * | 4/1996 | Imai et al. | 218/143 |
| 5,520,740 A * | 5/1996 | Kanai et al. | 118/723 |
| 5,549,802 A | 8/1996 | Guo | |
| 5,587,039 A | 12/1996 | Salimian et al. | |
| 5,714,010 A * | 2/1998 | Matsuyama et al. | 118/723 MW |
| 5,840,434 A * | 11/1998 | Kojima et al. | 427/456 |
| 5,858,100 A | 1/1999 | Maeda et al. | |
| 5,879,523 A | 3/1999 | Wang et al. | |
| 5,903,428 A | 5/1999 | Grimard et al. | |
| 5,910,338 A | 6/1999 | Donde | |
| 5,916,378 A | 6/1999 | Bailey et al. | |
| 5,916,454 A | 6/1999 | Richardson et al. | |
| 5,939,146 A * | 8/1999 | Lavernia | 427/446 |

(Continued)

FOREIGN PATENT DOCUMENTS

WO 9917336 4/1999

OTHER PUBLICATIONS

U.S. Appl. No. 60/304,091, Gell et al., filed Jul. 9, 2001.*

(Continued)

*Primary Examiner*—Marianne Padgett
(74) *Attorney, Agent, or Firm*—Janah & Associates

(57) ABSTRACT

A component for a substrate processing chamber comprises a structure having a textured coating with surface grains. The component is evaluated by directing a beam of electrons onto the textured coating of the component to cause at least some of the electrons to be backscattered. The backscattered electrons are detected and a signal image is generated. The component is selected when the signal image exhibits surface grains sized from about 0.1 to about 5 micron. In one version, the component is also selected when the grains are substantially flower shaped.

17 Claims, 9 Drawing Sheets

U.S. PATENT DOCUMENTS

| | | |
|---|---|---|
| 5,953,827 A | 9/1999 | Or et al. |
| 5,976,327 A | 11/1999 | Tanaka |
| 6,015,465 A | 1/2000 | Kholodenko et al. |
| 6,051,114 A | 4/2000 | Yao et al. |
| 6,059,945 A | 5/2000 | Fu et al. |
| 6,338,906 B1 | 1/2002 | Ritland et al. |
| 6,444,083 B1* | 9/2002 | Steger et al. ............... 118/715 |
| 6,773,751 B1* | 8/2004 | O'Donnell et al. .... 427/255.38 |
| 6,777,045 B1* | 8/2004 | Lin et al. ................... 428/34.6 |
| 2001/0033706 A1 | 10/2001 | Shimomura et al. |
| 2002/0086118 A1 | 7/2002 | Chang et al. |
| 2003/0026917 A1* | 2/2003 | Lin et al. .................... 407/453 |
| 2003/0108680 A1* | 6/2003 | Gell et al. ................. 427/446 |

OTHER PUBLICATIONS

Abstracts & Japan, 5416296A to Nagata Kazushi published application Dec. 25, 1979.

* cited by examiner

EVALUATION OF CHAMBER COMPONENTS HAVING TEXTURED COATINGS

BACKGROUND

Embodiments of the present invention relate to the evaluation of chamber components having textured coatings for substrate processing chambers.

A substrate processing chamber may be used to process a substrate with an energized process gas, such as a plasma. Typically, the process chamber comprises an enclosure wall that encloses a process zone into which a gas may be introduced, a gas energizer to energize a gas, and an exhaust to exhaust the gas. The process chamber may, for example, be used to deposit material on a substrate or etch material from a substrate. For example, the chamber may be used to sputter-etch material from a substrate or sputter-deposit material onto the substrate.

The chamber components exposed to the energized gas, such as for example, the sidewall or ceiling of the chamber, or the liner or focus ring about the substrate, are often coated with a textured coating to enhance the adhesion of the sputtered residues on the component. For example, a suitable chamber may be made from aluminum or quartz and coated with a plasma sprayed coating of aluminum oxide or alumino-silicate, as for example, described in commonly assigned U.S. Pat. No. 6,777,045, application Ser. No. 09/895,862 filed Jun. 27th, 2001, entitled A Chamber Having Components with Textured Surfaces and Method of Manufacture, A by Lin et al., which is incorporated herein by reference in its entirety. The coating enhances adhesion of residues which are formed in the chamber, such as for example, sputtering residues that are formed when the components are used in chambers in which a target is sputtered to deposit material onto a substrate. Without the coating, the residues that accumulate on the component over a number of process cycles, would eventually flake-off and fall upon and contaminate the substrate.

While chambers having the coated components generally provide better substrate yields and require less frequent chamber cleaning, sometimes, the sputtered residues accumulated on the coated component can cause the entire underlying coating to delaminate and peel-off the component. Such components are undesirable because they reduce the ultimate yield from the substrates being processed in the chamber due to contamination of the substrate by the peeled off coating flakes. However, current component fabrication and evaluation methods often fail to identify or separate those components that are able to withstand accumulation of the sputtered residues without delaminating from those components that cannot withstand excessive accumulate deposits.

Thus, it is desirable to have a method of fabricating and selecting chamber components having desirable coating characteristics. It is also desirable for the components to provide superior adhesion of process residues, such as sputtering residues, in a substrate processing chamber.

SUMMARY

A method of selecting a component for a substrate processing chamber, the method comprising:
(a) providing a structure having a textured coating having surface grains; and
(b) evaluating the textured coating on the structure by:
  (i) directing a beam of electrons onto the surface grains of the textured coating thereby causing at least some of the electrons to be backscattered,
  (ii) detecting the backscattered electrons and generating a signal image,
  (iii) evaluating the signal image to determine the size of the surface grains of the textured coating, and
  (iv) selecting the component when the surface grains of the textured coating are sized from about 0.1 to about 5 micron.

A method of selecting a component for a substrate processing chamber, the method comprising:
(a) providing a structure having:
  (i) a shape suitable for a chamber enclosure wall, gas shield, cover ring or deposition ring, the structure being made from stainless steel, aluminum, titanium, copper, copper alloy, quartz or aluminum oxide; and
  (ii) a plasma sprayed coating or a thermal sprayed textured coating on the shape, the textured coating having surface grains comprising one or more of aluminum, silicon, aluminum oxide, boron carbide and titanium oxide; and
(b) evaluating the textured coating by:
  (i) directing a beam of electrons onto the surface grains of the textured coating thereby causing at least some of the electrons to be backscattered,
  (ii) detecting the backscattered electrons and generating a signal image,
  (iii) evaluating the signal image to determine the size of the surface grains of the textured coating, and
  (iv) selecting the component when the surface grains of the textured coating are sized from about 0.1 to about 5 micron and are substantially flower shaped.

A substrate processing chamber component comprising a structure and a textured coating on the structure, the textured coating consisting essentially of surface grains sized from about 0.1 to about 5 micron. The structure may be shaped to be a chamber enclosure wall, gas shield, cover ring or deposition ring, the structure made from stainless steel, aluminum, titanium, copper, copper alloy, quartz or aluminum oxide. The textured coating may be made from aluminum, silicon, aluminum oxide, boron carbide or titanium oxide. The substrate processing chamber having the component may include a gas supply to provide a process gas into the chamber, a plasma generator to form a plasma of the process gas in the chamber to process the substrate, and a gas exhaust to exhaust the process gas.

DRAWINGS

These features, aspects, and advantages of the present invention will become better understood with regard to the following description, appended claims, and accompanying drawings which illustrate examples of the invention. However, it is to be understood that each of the features can be used in the invention in general, not merely in the context of the particular drawings, and the invention includes any combination of these features, where:

Figure 8:
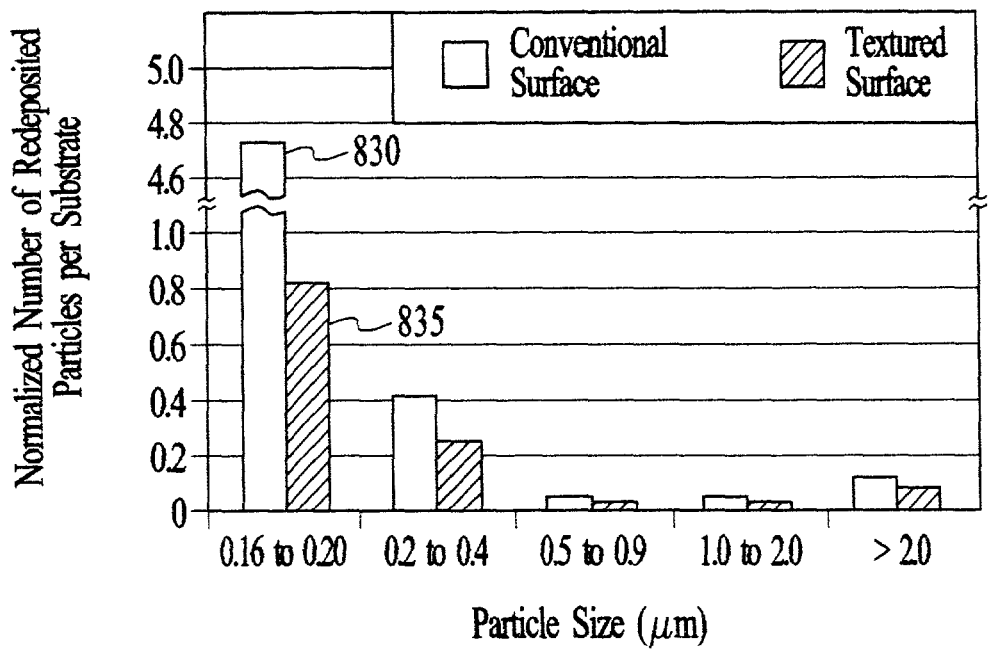
Figure 9:
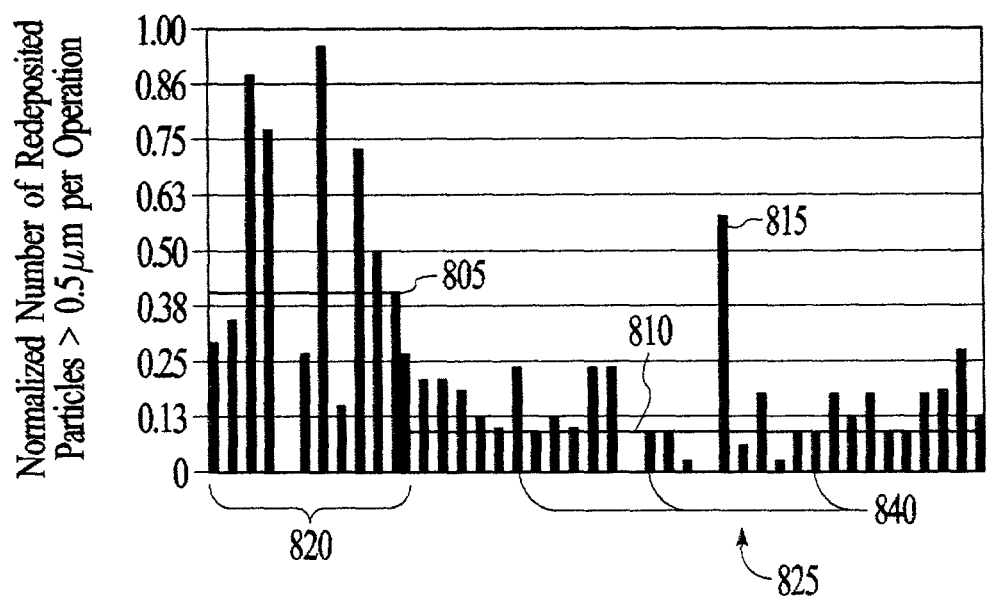

FIG. 8 is a comparative bar graph of a normalized number of redeposited particles measured per substrate, at different particle size ranges, for substrates processed in chambers having conventional components and chambers having components according to the present invention; and FIG. 9 is a comparative bar graph of a normalized number of redeposited particles greater than 0.5 micrometers obtained per cycle in chambers having conventional components and components according to the present invention.

DESCRIPTION

Figure 1:
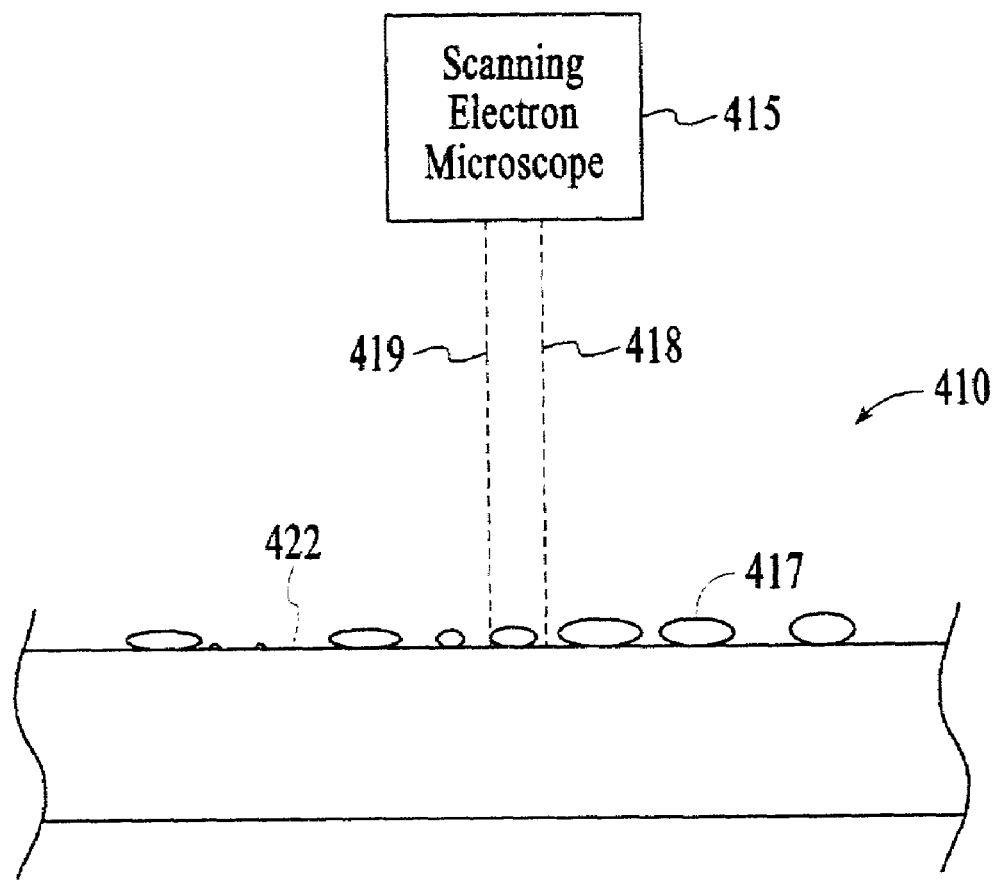
FIG. 1 is a cross-sectional view of a component having a surface comprising grains.

A component 410 suitable for use in a substrate processing environment, such as a plasma sputtering environment, may be fabricated according to the present method. In the fabrication method, electrons are backscattered from a surface 422 of a component 410 to generate a signal image to allow the selection of components 410 that exhibit specific properties that can provide improved adhesion and retention of process residues such as sputtered materials 423 to the surface 422 of the component 410 in the processing of a substrate. In the method, a beam of electrons 418 is directed onto the surface 422 and at least some of the incident electrons are reflected or backscattered from the surface 422 as for example, illustrated in FIG. 1. The backscattered electrons 419 comprise electrons that are scattered away from the surface 422 by elastic or inelastic electron interactions between atoms on the surface 422 and the incident electrons. The incident electron beam 418 may be generated by, for example, a scanning electron microscope 415, which may also be used to detect the backscattered electrons. A signal image is generated in relation to the detected backscattered electrons 419 that corresponds to the topography of the surface 422 and allows for analysis of the surface 422. For example, the signal image may comprises variations in image contrast that correspond to the surface topography. Accordingly, the signal image may be evaluated to select components 410 comprising the desired surface properties, such as a desired surface morphology.

In one version, the signal image may be evaluated to select components 410 having a surface 422 comprising surface grains 417 having a desired range of sizes. The surface grains 417 are the grains at surface of the surface 422 which may have other layers of grains inside the coating. The size of surface grains 417 affect the adherence and retention of sputtered particles to the surface 422, thereby affecting the performance of the chamber 100 using the component and the yield of substrates 110 processed in the chamber 100. For example, a surface 422 having larger surface grains 417 may provide a surface morphology comprising concavities 424 and valleys between the grains 417, such as those shown in FIG. 3, that allow the accumulation of sputtered materials 423 on the textured exposed surface 422 with reduced flaking of the sputtered materials from the surface 422. A surface 422 defined by smaller surface grains 417, on the other hand, may have fewer or smaller concavities 424 that may not accommodate the sputtered materials 423. Also, the size of the surface grains 417 can affect the behavior of the surface under thermal expansion stresses, with an optimal size range providing good adhesion between the grains 417 and the underlying component 410. Accordingly, in one version, the component 410 is selected by evaluating the signal image to determine whether the surface 422 has surface grains 417 that are within a range of sizes. For example, the signal image may be evaluated to select a component 410 comprising a surface 422 having surface grains 417 that are sized from about 0.1 to about 5 microns. In one version, the signal image may even be evaluated to select a component 410 comprising a surface 422 consisting essentially of surface grains 417 that are sized from about 0.1 to about 5 microns.

Figure 2B:
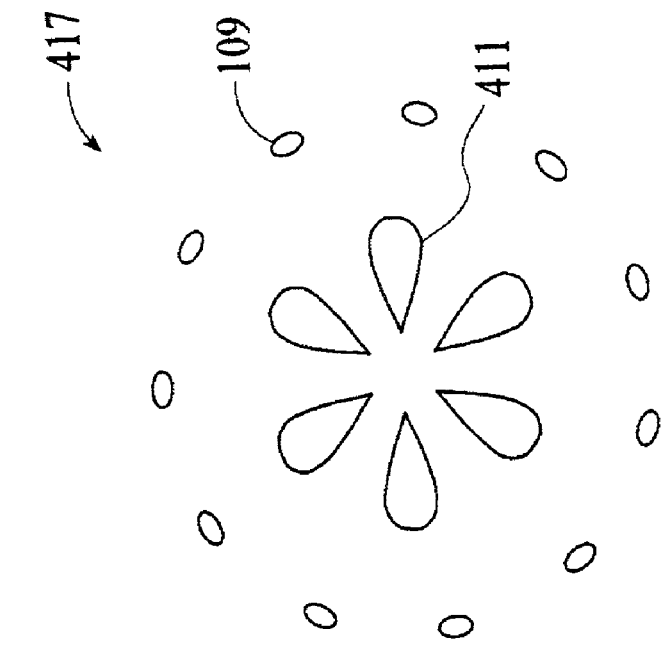
FIGS. 2a and 2b are views of lamella patterns of grains of the textured coating.
Figure 2A:
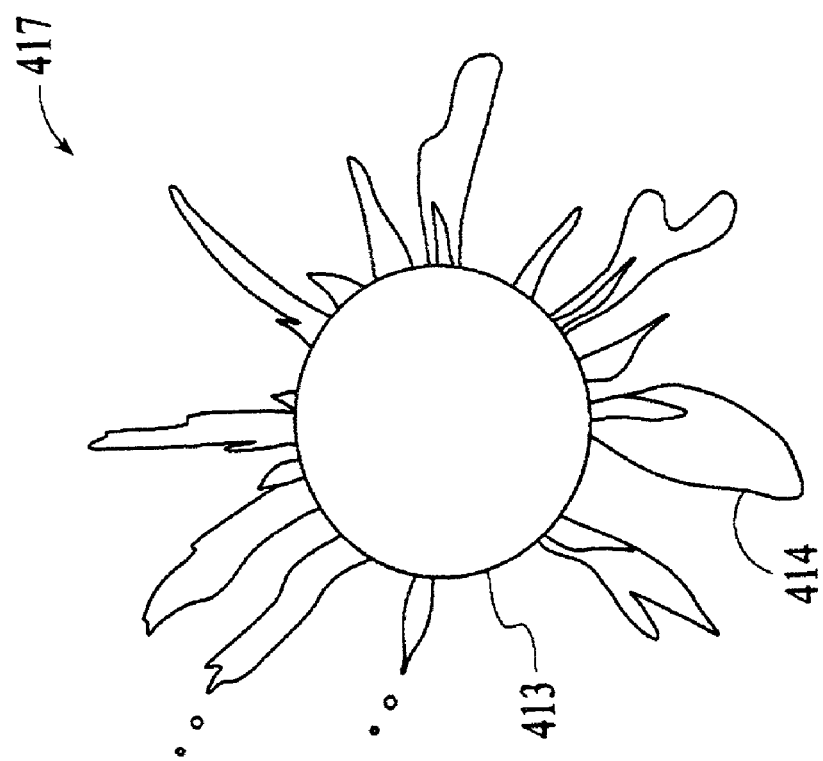

The signal image may also be evaluated to select components 410 having a surface 422 comprising surface grains 417 having a desired shape. It has been discovered that surfaces 422 comprising surface grains 417 with different morphological forms have varying degrees of adherence and retention of sputtered materials 423 in the chamber 100. For example, a surface 422 comprising surface grains 417 having a substantially flower type shape, as shown in FIG. 2b, provides improved adherence to sputtered material over a surface 422 comprising grains 417 having a pancake type shape, as shown in FIG. 2a. The flower shaped grains 417 generally comprise a cluster of petals 411 encircled by a ring of small particles 109 that provide concavities 424 and crevices in between the petals 411 and small particles 109 that are suitable for the accumulation of sputtered material. In contrast, the pancake shaped grains 417 generally comprise a large radially symmetric central portion 413 with outwardly radiating ridges 414, and thus provide fewer and less suitable concavities 424 and crevices. Accordingly, in one version, a signal image generated in relation to the detected backscattered electrons may be evaluated to select components 410 comprising a surface 422 having grains 417 that are substantially flower shaped, as in FIG. 2b.

Figure 3:
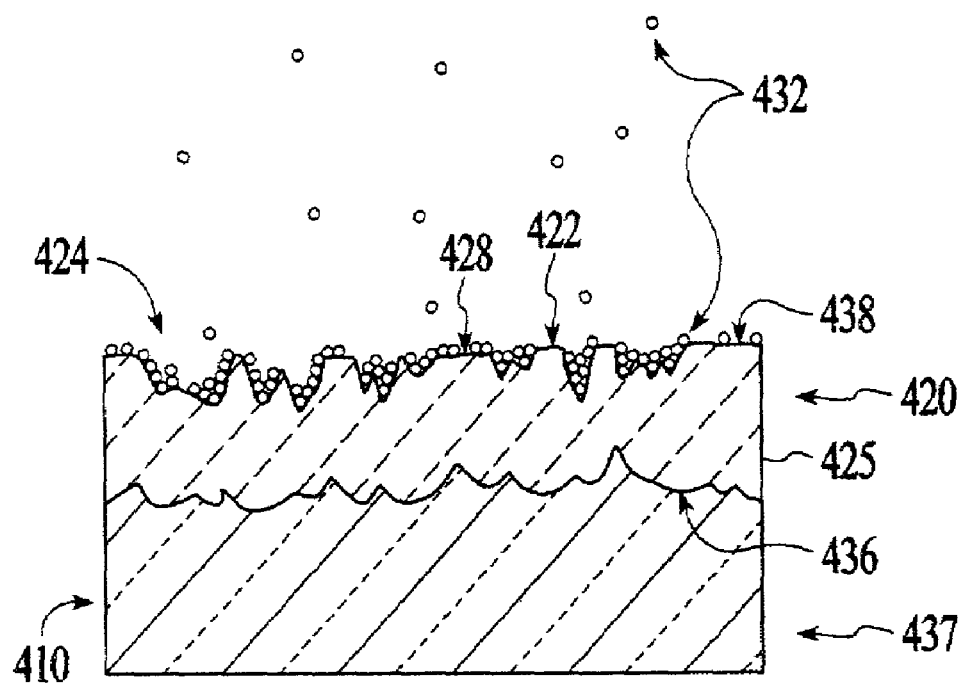
FIG. 3 is a cross-sectional partial view of a component having a surface with a surface roughness having a negative skewness and showing the adhesion of sputtered particles to the surface.

The component 410 may be further selected by evaluating surface profile parameters such as the average surface roughness and skewness of the surface 422. For example, a component 410 may be selected if it has a surface 422 having a roughness with a skewness that significantly and unexpectedly improves the adhesion and retention of sputtered materials 423 onto the textured exposed surface 422, as illustrated in FIG. 3. The skewness (Rsk) is determined using the following formula:

$$R_{sk} = \frac{1}{R_q^3} \frac{1}{N} \sum_{j=1}^{N} Z_j^3$$

$$\text{where } R_q = \sqrt{\frac{\sum_{i=1}^{N} Z_i^2}{N}}$$

is the root mean square roughness of the surface 422, N is a number of sample points of the surface 422 used to make each skewness measurement, and $Z_1, Z_2, \ldots Z_N$ are the height deviations from the mean line measured at the sample points. The skewness is a measure of the asymmetry of the surface profile about the mean line. A surface having negative skewness 422, as shown in FIG. 3, has concavities 424, such as pits or valleys, extending into the surface 422, and may also have substantially flat areas 428 distributed between mainly concavities 424. In one version, the skewness should be sufficiently negative to allow the sputtered or other material that is formed in the chamber to contact and adhere to the surface 422. Suitable skewness values can range from about −0.7 to about 0.1, or even from about −0.5 to about 0.

In one embodiment, the component is selected to have an average skewness of the surface 422, which represents the average of a number of measured skewness values across the surface 422, that is a negative value (less than zero) such as less than about −0.1. The negative average skewness of the surface 422 provides a surface morphology that has been found to unexpectedly improve the adhesion and retention of sputter etched and other particles formed in a chamber using the component 410 to thereby improve chamber performance and substrate yields. While it is desirable for the average skewness value to be negative, it should be understood that individually measured skewness values may be negative or may be positive, so long as the average of a number of such individual values is a negative value. It is believed that a surface 422 having a negative average skewness promotes adhesion of the particulate matter formed in the chamber 100, such as sputter etched particles 423, by allowing troughs and valleys present in such a surface 422 to have a better grip on the particles.

Another property that may be used to evaluate the surface 422 is the roughness average (Ra) of the surface of the surface 422 that is the mean of the absolute values of the displacements from the mean line of the peaks and valleys of the roughness features along the surface 422. The roughness average, skewness, or other properties may be determined by a profilometer that passes a stylus over the surface 422 and generates a trace of the fluctuations of the height of the asperities on the surface 422, or by a scanning electron microscope that detects electrons backscattered from the surface 422 to generate an image of the surface 422. In one version, a component 410 is cut into coupons (not shown), and one or more measurements are made at each coupon to determine the skewness of each coupon. These skewness measurements are then averaged to determine an average skewness of the surface 422. The average skewness of the surface 422 that is a negative value was found to significantly improve the adhesion and retention of sputtered material. In one version, a suitable roughness average value may be from about 150 microinches (∼3.8 micrometers) to about 450 microinches (∼11.4 micrometers), or from about 300 microinches (∼7.6 micrometers) to about 450 microinches (∼11.4 micrometers). In another version, a suitable roughness average value may be from about 700 microinches (∼17.8 micrometers) to about 900 microinches (∼23 micrometers). In yet another version, a suitable average roughness value may be from about 1100 microinches (∼28 micrometers) to about 1450 microinches (∼36.8 micrometers).

Yet another property of the surface 422 that may be evaluated to select the component 410 is the average peak slope value of the surface roughness (Rda). In one embodiment, the average peak slope value of the surface 422 may be selected to be from about 20 to about 25. Yet another evaluated property may be a measurement of the number of surface peaks that exceed the height of a mean height line through the roughness peaks and valleys (Rpc). For example, the value of the peaks over the mean line for the surface 422 may be selected to be from about 175 to about 225. Yet another property may be a measurement of the sharpness of the surface profile (Rku). For example, the value of the sharpness of the surface profile may be from about 2.5 to about 4.0.

In measuring properties of the surface 422 such as roughness average, skewness, or other characteristics, the international standard ANSI/ASME B.46.1-1995 specifying appropriate cut-off lengths and evaluation lengths, can be used. The following Table I shows the correspondence between values of roughness average, appropriate cut-off length, and minimum and typical evaluation length as defined by this standard:

TABLE I

| Roughness Average | Cut-off Length | Min. Evaluation Length | Typ. Evaluation Length |
|---|---|---|---|
| 0 to 0.8 microinches | 0.003 inches | 0.016 inches | 0.016 inches |
| 0.8 to 4 microinches | 0.010 inches | 0.050 inches | 0.050 inches |
| 4 to 80 microinches | 0.030 inches | 0.160 inches | 0.160 inches |
| 80 to 400 microinches | 0.100 inches | 0.300 inches | 0.500 inches |
| 400 microinches and above | 0.300 inches | 0.900 inches | 1.600 inches |

Figure 7A:
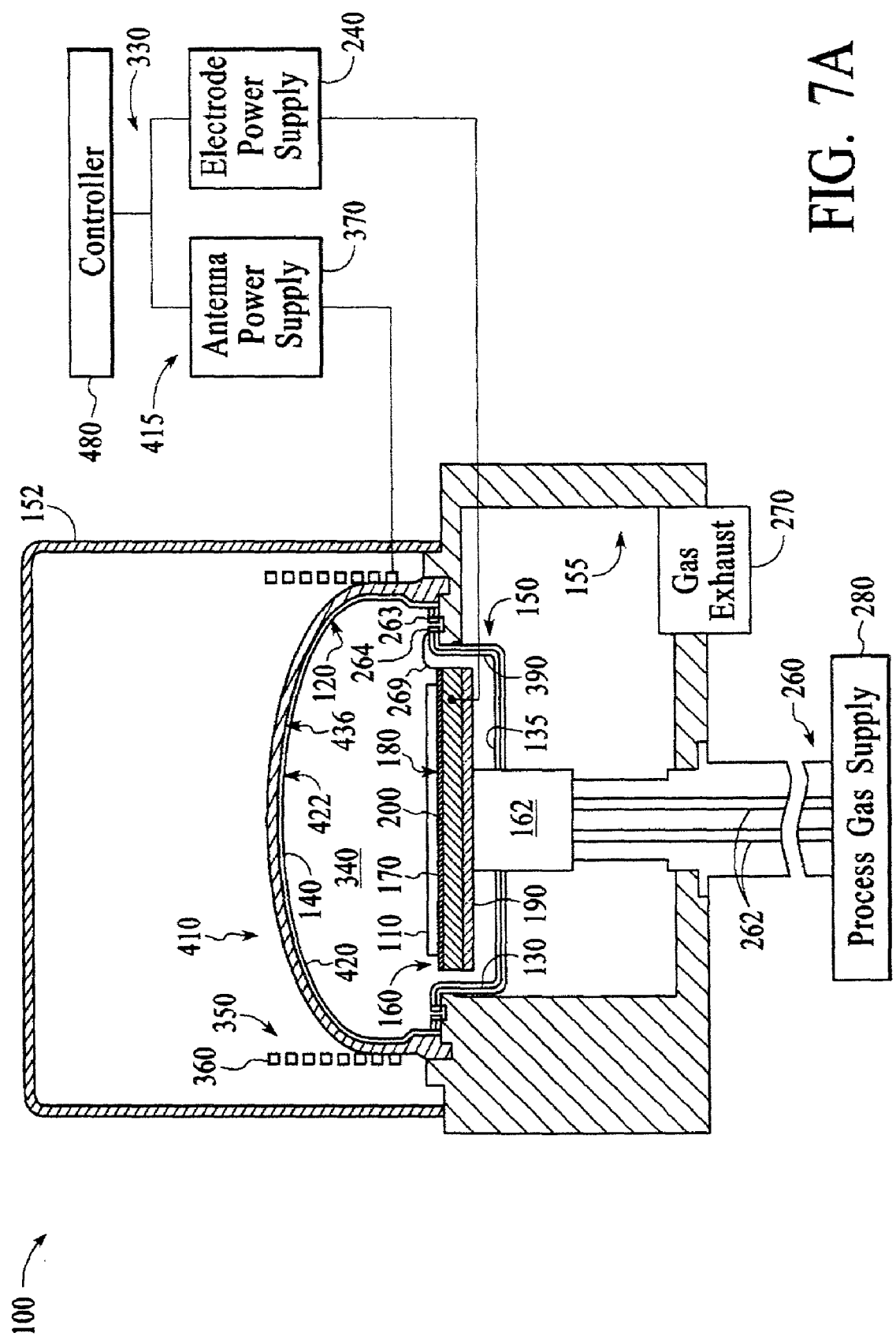
FIG. 7a is a process chamber according to an embodiment of the present invention.
Figure 7B:
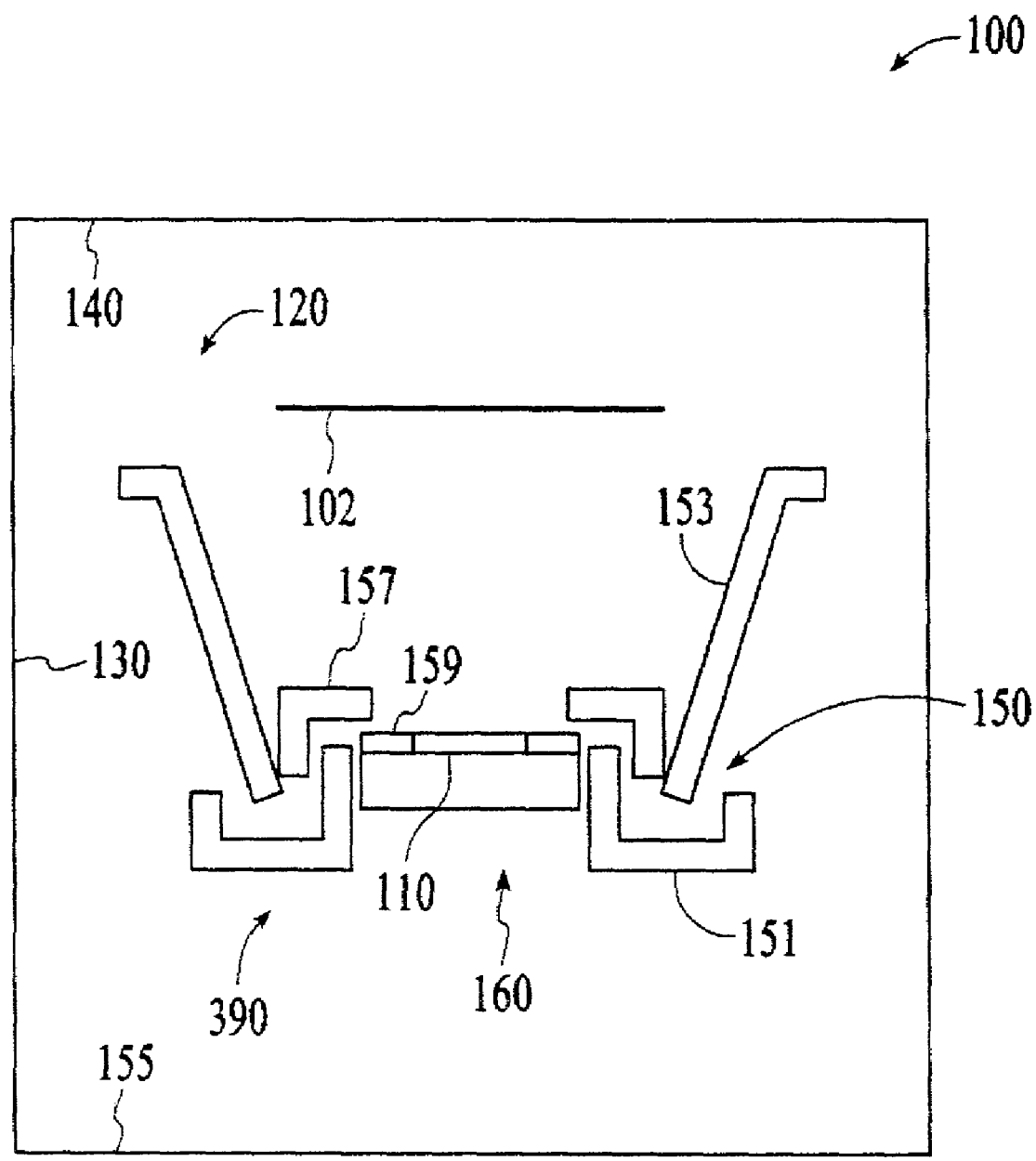
FIG. 7b is a cross-sectional partial view of an embodiment of a gas shield and annular rings about a substrate support.

The surface 422 is typically that of a textured coating 420 formed over an underlying structure 437 of the component 410, as shown for example in FIG. 3. The textured coating 420 is often at least partially exposed to an energized gas formed in a process chamber 100 and, thus, may be selected to provide improved erosion resistance to protect the underlying structure 437. In one version, the component 410 comprises a portion of a gas shield 150, such as a lower shield 151 or upper shield 153, used to protect walls of the chamber 100 from erosion, as shown in FIGS. 7a and 7b. In another version, the component 410 comprises one or more annular rings 390 that are positioned about the substrate support 160, such as a cover ring 157 and deposition ring 159, as shown in FIG. 7b. In yet another version, the component 410 comprises a domed enclosure wall 120 that serves as a ceiling 140 of the chamber 100, as shown in FIG. 7a.

The underlying structure 437 of the component 410 is formed by shaping a dielectric material or conductor material. The dielectric material may be permeable to RF energy to pass RF energy from a plasma generator 330. The dielectric material may also be a ceramic. In one method of fabrication, the underlying structure 437 is formed by shaping a mixture of ceramic powders and a binder such as an organic binder. The ceramic powder and binder may be filled into a mold to form a suitable ceramic preform by, for example, slip casting, ram pressing, or isostatic pressing, or may be formed by tape casting. Thereafter, the shaped preform is sintered to form a hardened ceramic material comprising the underlying structure 437 that may be further shaped by machining. Suitable ceramic materials include quartz and aluminum oxide. An exemplary component 410 comprising the dielectric underlying structure 437 is the domed enclosure wall 120 that serves as the ceiling 140, and that is made from a material such as quartz.

The underlying structure 437 may also be formed from a metal. For example, a metal composition may be heated to form a molten metal or metal alloy that is poured into a mold comprising the desired component shape. The molten metal is allowed to cool in the mold to form the metal underlying structure 437. Metals that are suitable for forming the underlying structure 437 may comprise, for example, one or more of stainless steel, aluminum, titanium, copper and copper alloys. Exemplary components 410 comprising the metal underlying structure 437 are one or more of the gas shield 150, deposition ring 159 and cover ring 157 that are made from a material such as stainless steel.

Figure 4A:
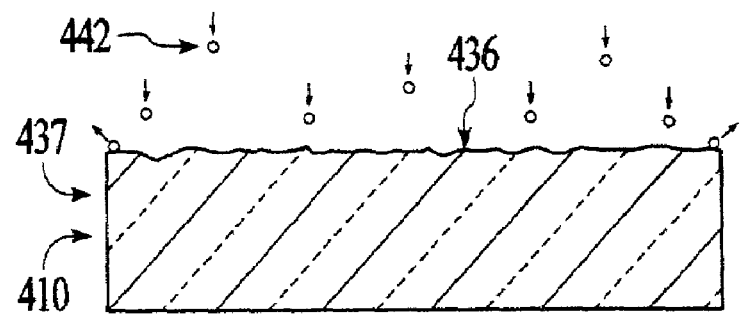
FIG. 4a is a cross-sectional view of a roughened surface of a component.
Figure 4B:
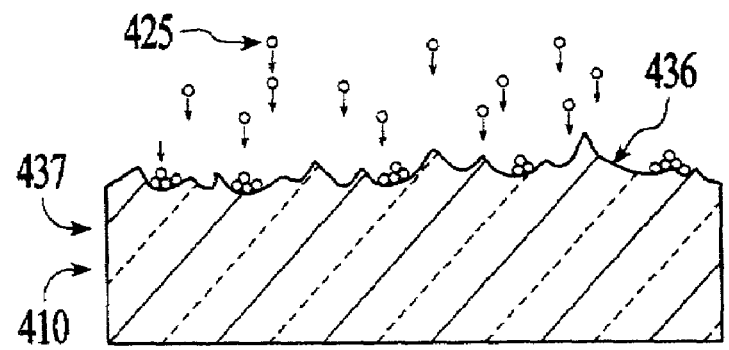
FIG. 4b is a cross-sectional view of the component of FIG. 4a after the surface has been roughened and while a coating is being applied thereto.
Figure 4C:
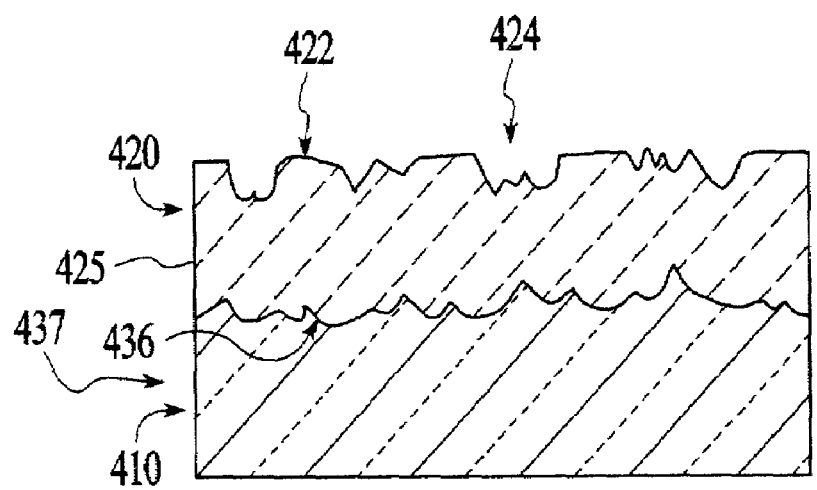
FIG. 4c is a cross-sectional view of the final surface of the component of FIG. 4b.

In one version, the textured coating 420 comprising the surface 422 to be evaluated is applied to the underlying structure 437 as illustrated in FIGS. 4a to 4c. Prior to the application of the textured coating 420, the underlying surface 436 of the structure 437 is typically smooth, as shown in FIG. 4a. The underlying surface 436 is then roughened, for example by bead blasting. Roughening of the underlying surface 436 may provide a basis for the characteristics of the surface morphology of the overlying textured coating 420, or may serve to activate the underlying surface 463 to promote better adhesion of the textured coating 420. In bead blasting, solid beads 442 are propelled toward the surface 436 by air at a pressure that is sufficiently high to suitably roughen the surface 436, such as for example, a pressure of from about 40 to about 50 pounds per square inch (psi). Also, the angle of incidence of the beads 442 relative to the surface 436 is selected to roughen the surface 436 to promote adherence of the final textured coating 420 to the surface 436. For example, a suitable angle of incidence may be from about 30 degrees to about 60 degrees, or even about 45 degrees.

In one embodiment, a bead blaster (not shown) in an enclosed housing is used to roughen the surface of the underlying structure 437. The beads may comprise a material having a hardness higher than that of the structure 437 to allow the beads to erode and roughen the surface of the structure 437 to form the roughened surface 436. Suitable bead materials include for example, alumina oxide, glass, silica, or hard plastic. In one embodiment, the beads comprise a grit of aluminum oxide having a mesh size selected to suitably grit blast the surface 436, such as for example, a grit of aluminum oxide particles having a mesh size of 36. In one version, a ceramic underlying surface 436 may be roughened to have a roughness average, of for example, from about 150 microinches (~3.8 micrometers) to about 450 microinches (~11.4 micrometers), or from about 300 microinches (~7.6 micrometers) to about 450 microinches (~11.4 micrometers). In another version, a metal underlying surface 436 may be roughened to have a roughness average of from about 100 microinches (~2.5 micrometers) to about 300 microinches (~7.6 micrometers), and even about 200 microinches (~5 micrometers). Additionally, the standoff distance traveled by the beads 442 from the bead blaster to the component is also set to provide the desired roughness of the surface 436. For example, the standoff distance may be from about 4 inches to about 6 inches from the bead blasting source to the component surface 436.

After bead blasting, the surface 436 is cleaned to improve the subsequent adhesion and retention of the coating material 420. For example, the surface 436 can be cleaned by blowing clean dry air or nitrogen gas across the surface 436. Subsequently, in one version, the surface 436 is further cleaned, for example chemically, using distilled water, or in an ultrasonic rinse. Additionally, the component 410 may be baked in an oven to bake out any residues, such as from the cleaning process. For example, the component surface 436 may be baked at a temperature of at least about 100° Celsius to improve the subsequent deposition of the coating material 420 onto the surface 436.

After cleaning of the component surface 436, a textured coating 420 is formed over the surface 436, as illustrated in FIG. 4b. The textured coating 420 may be applied by a method which provides a strong bond between the coating 304 and the underlying surface 436. For example, the textured coating 420 may be applied by one or more of a chemical or physical deposition process, or by a flame spraying or thermal spraying method, such as a twin wire arc method, plasma spray method, or oxy-fuel gas flame. The textured coating 420 may be made of a material 425, such as a ceramic material, such as for example one or more of aluminum oxide, titanium oxide and boron carbide, or may be made of a metal, such as for example one or more of aluminum and silicon.

The textured coating 420, shown in FIG. 3, may have a thickness suitable to avoid excessive outgassing. In one embodiment, the textured coating 420 has a thickness of less than about 20 mils (~508 micrometers), and even less than about 10 mils (~254 micrometers), for example, a thickness of from about 1 mil (~25 micrometers) to about 8 mils (~203 micrometers), or a thickness of from about 3 mils (~76 micrometers) to about 5 mils (~127 micrometers), or even a thickness of from about 6 mils (~152 micrometers) to about 9 mils (~229 micrometers).

The coating material 425 may also be tailored to have a porosity that is sufficiently high to promote the adherence of chamber generated particulate matter onto the surface 422. The porosity of the coating material 425 is the ratio of the volume of pore interstices to the volume of its mass. For example, the coating material 425 may have a porosity of from about 5% to about 10%, such as about 7%. In one version, it is desirable that the porosity not exceed about 7% to promote optimum adhesion of the textured coating 420 to the underlying surface 436.

Figure 5:
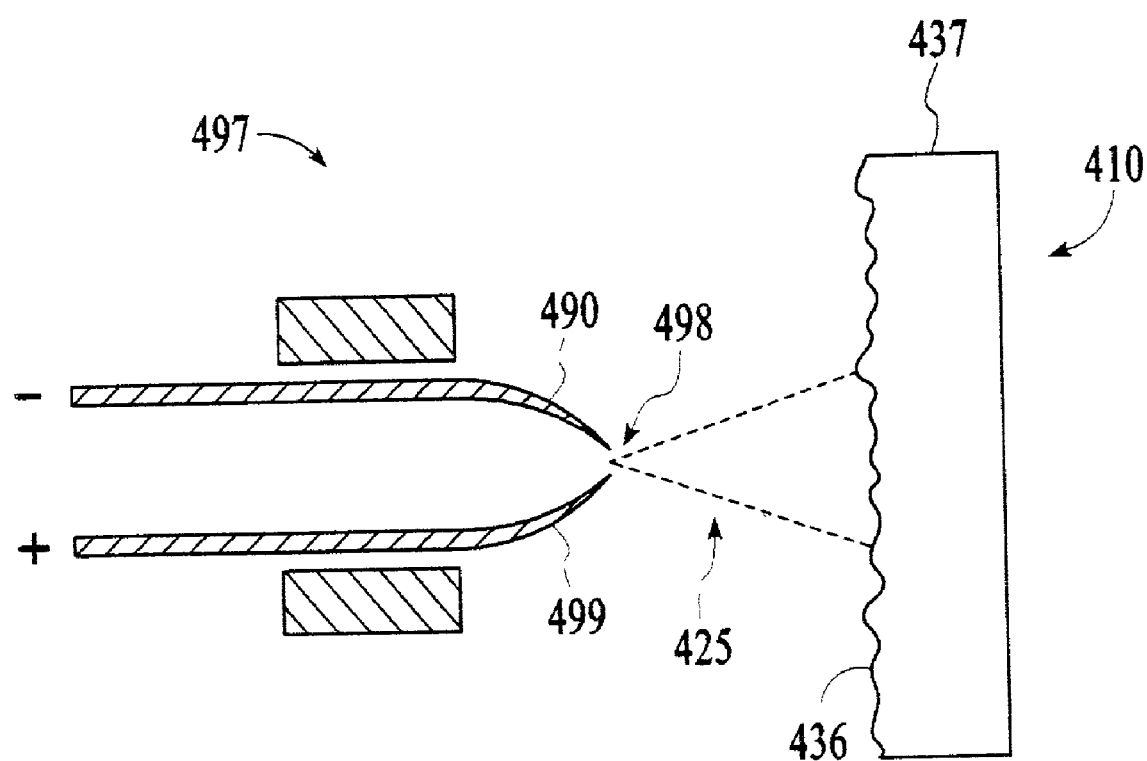
FIG. 5 is a cross-sectional view of a twin wire arc thermal sprayer spraying a coating onto a roughened surface of a component structure.

In one version, the textured coating 420 is applied to the surface 436 by a thermal spraying process, such as a twin wire arc spraying process, as for example, described in U.S. Pat. No. 6,227,435 B1, issued on May 8$^{th}$, 2001 to Lazarz et al, and U.S. Pat. No. 5,695,825 issued on Dec. 9$^{th}$, 1997 to Scruggs, both of which are incorporated herein by reference in their entireties. For example, in one exemplary version, one or more of the gas shield 150, deposition ring 159 and cover ring 157 comprises a textured coating 420 of aluminum sprayed using a twin wire arc spraying process onto an underlying structure 437 comprising stainless steel. In the twin wire arc spraying process, a twin wire arc sprayer 497 comprises two consumable electrodes 490, 499 that are shaped and angled to allow an electric arc 498 to form therebetween, as shown for example in FIG. 5. For example, the consumable electrodes 490, 499 may comprise twin wires formed from a metal to be coated on the surface 306, which are angled towards each other to allow an electric discharge to form near the closest point. An electric arc discharge is generated between the consumable electrodes 490, 499 when a voltage is applied to the consumable electrodes 490, 499 as a carrier gas, such as one or more of air, nitrogen or argon, is flowed between the electrodes 490, 499. Arcing between the electrodes atomizes and at least partially liquifies the metal on the electrodes 490, 499, forming molten coating material 425, and carrier gas energized by the arcing electrodes propels the molten particles out of the thermal sprayer 497 and towards the surface 436 of the component 410. The molten particles impinge on the surface 436, where they cool and condense to form a conformal textured coating 420, as shown in FIG. 4c. When twin wires are used, the wires may be continuously fed into the thermal sprayer to provide a continuous supply of the metal material.

Figure 6:
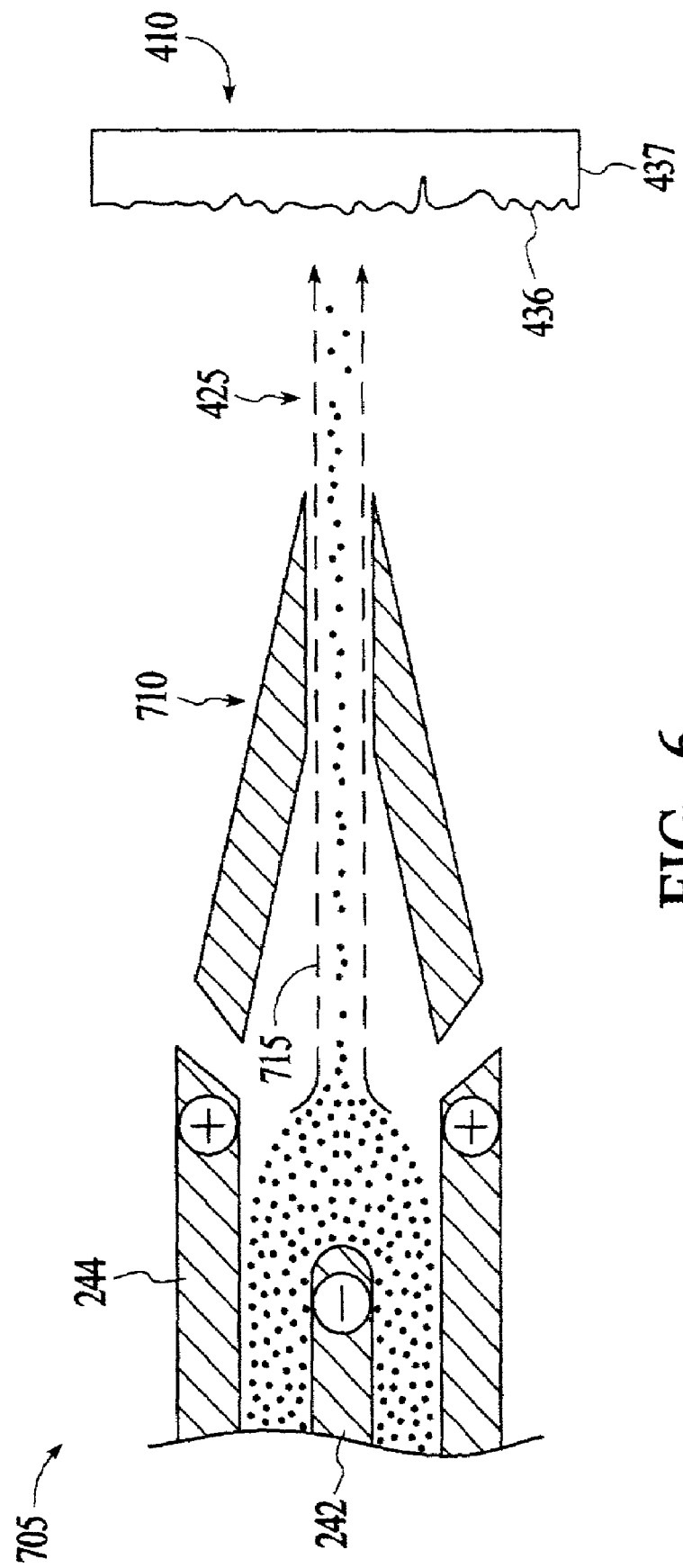
FIG. 6 is a cross-sectional view of a plasma torch depositing a coating material on a roughened surface of a component structure.

In another version, the textured coating 420 is applied to the surface 436 by a plasma spraying process. For example, in one exemplary version, the domed enclosure wall 120 comprises a textured coating 420 of aluminum oxide plasma sprayed over an underlying structure 437 comprising quartz. In plasma spraying, a plasma is formed to atomize and at least partially liquefy a spray of particulate coating material 425 injected through the plasma. For example, the plasma may liquefy the coating material 425 by heating the coating material 425 to a temperature of thousands of degrees Celsius. The liquified droplets of the coating material 425 impinge at high velocities on the roughened underlying surface 436 and rapidly solidify to form a conformal textured coating 420, as shown in FIG. 4c. In one version, a plasma spray torch 705 is used to plasma spray the coating material 425 onto the surface 436, as shown in FIG. 6. The plasma torch 705 may be mounted on a controllable robotic arm (not shown) to adjust the distance and angle of the plasm torch 705 from the surface 436. Also, the plasma torch 705 may be inside a chamber (not shown) to control the gas environment in which the plasma torch 705 is immersed.

In the plasma torch 705, a carrier gas is flowed between two electrodes, such as a cathode 242 and an anode 244. The carrier gas is suitable to form a high-pressure plasma, such as argon, nitrogen, hydrogen, or helium. Argon may be used because it is chemically inert and because of its ionization characteristics. Adding diatomic gases, such as hydrogen or nitrogen, can increase the enthalpy of the gas. The cathode 242 and anode 244 comprise materials suitable to generate an electric discharge arc through the plasma, such as metals like tungsten or copper. In one embodiment, the cathode 242 is made of tungsten and the anode 244 is made of copper. Additionally, in one version, the anode is cooled, for example water-cooled, to prevent overheating. The cathode 242 and the anode 244 may be correspondingly shaped to suitably generate an electric arc between them. For example, the cathode 242 may be cone-shaped and the anode 244 may be cylindrical.

An AC high-frequency discharge initiates an electric arc between the cathode 242 and the anode 244 and is sustained using DC power. The electric arc ionizes the carrier gas, creating a high-pressure plasma. The resulting increase in gas temperature increases the volume of the gas and, thus, the pressure and velocity of the gas as it exits a nozzle 710. The coating material 425 is introduced into the gas stream 715 in powder form. The powdered coating material 425 can be introduced just outside the plasma torch 705 or in the diverging exit region of the nozzle 710. The coating material 425 is heated and accelerated by the high-temperature, high-velocity plasma stream.

Operating parameters of the plasma torch 705 or twin wire arc sprayer 497 are selected to be suitable to adjust the characteristics of the coating material application, such as the temperature and velocity of the coating material 425 as it traverses the path from the plasma torch 705 or twin wire arc sprayer 497 to the component surface 436. For example, gas flow rates, power levels, powder feed rate, carrier gas flow, standoff distance from the plasma torch 705 or twin wire arc sprayer 497 to the surface 436, and the angle of deposition of the coating material 425 relative to the component surface 436 can be adapted to improve the application of the coating material 425 and the subsequent adherence of the textured coating 420 to sputtered material. For example, in the plasma torch 705, the voltage between the cathode 242 and the anode 244 may be selected to be from about 30 Volts to about 60 Volts, such as about 45 Volts. Additionally, the current that flows between the cathode 242 and the anode 244 may be selected to be from about 500 Amps to about 700 Amps, such as about 600 Amps. The power level of the plasma torch 705 is usually in the range of from about 12 to about 120 kilowatts, such as about 80 kilowatts. In the twin wire arc sprayer 497, the voltage between the consumable electrodes 490, 499 may be selected to be from about 30 to about 32 volts, such as 31 volts. The current that flows between the consumable electrodes 490, 499 may be selected to be from about 50 Amps to about 200 Amps, such as about 100 Amps. The pressure of carrier gas flowing through the twin wire arc sprayer 497 may be from about 25 to about 75 psi, such as about 50 psi.

The standoff distance and angle of deposition can be selected to adjust the deposition characteristics of the coating material 425 on the surface 436. The standoff distance and angle of deposition can be adjusted to modify the phase, velocity, or droplet size of the coating material 425 when it impacts the surface 436. In one embodiment, the standoff distance between the plasma torch 705 and the surface 436 is from about 2 inches to about 4 inches, such as about 3 inches. The angle of deposition of the coating material 425 onto the surface 436 may be from about 75 degrees to about 105 degrees relative to the surface 436, such as about 90 degrees. In another embodiment, the standoff distance between the twin wire arc sprayer 497 and the surface 436 is from about 2 inches to about 6 inches, such as about 4 inches. In this embodiment, the angle of deposition of the coating material 425 onto the surface 436 may be from about 60 degrees to about 100 degrees relative to the surface 436, such as about 90 degrees.

The velocity of the coating material 425 can be adjusted to suitably deposit the coating material 425 on the surface 436. In one embodiment, the velocity of the coating material 425 form the plasma torch 750 or twin wire arc sprayer is from about 300 to about 550 meters/second. Also, the plasma torch 705 or thermal sprayer 497 may be adapted so that the temperature of the coating material 425 is at least about the melting temperature of the coating material 425 when the coating material 425 impacts the component surface 436. Temperatures above the melting point can yield a textured coating 420 of high density and bonding strength. For example, the temperature of the plasma may exceed 30,000° C. In one embodiment the bonding strength is from about 29 MPa to about 75 MPa. However, the temperature of the plasma about the electric discharge can also be set to be sufficiently low that the coating material 425 remains molten for a period of time upon impact with the component surface 436. For example, an appropriate period of time may be at least about 0.02 seconds or at least about 0.1 seconds.

The velocity and temperature of the coating material 425 also affects the coating morphology. For example higher coating material velocities and temperatures may yield a textured coating 420 comprising more of the flower shaped grains, whereas lower coating material temperatures and velocities may yield a textured coating 420 comprising more of the pancake shaped grains. Furthermore, the temperature of the surface 436 may also be controlled to provide desirable coating characteristics.

Once the textured coating 420 has been applied, the surface 422 of the coating is evaluated by detecting electrons backscattered from the surface 422 to determine whether the surface comprises, for example, grains 417 having a suitable size and shape. Detection of the backscattered electrons to determine grain size and shape may also be performed in combination with the evaluation of other surface profile parameters, such as the average surface roughness and surface skewness, to provide an improved multiparameter analysis of the component surface 422. As an example, Table 2 below demonstrates the range of surface properties evaluated for two different coated components 410 suitable for use in a substrate processing chamber 100, the coated components 410 comprising (1) a component 410 comprising an aluminum oxide textured coating 420 plasma sprayed onto an underlying structure 427 comprising quartz, and (2) a component 410 comprising an aluminum textured coating 420 sprayed using a twin wire arc thermal spraying process onto an underlying structure 437 comprising stainless steel.

TABLE 2

| | $R_a$ | $R_{sk}$ | $R_{da}$ | $R_{ku}$ | $R_{pc}$ |
|---|---|---|---|---|---|
| (1) Plasma Spray $Al_2O_3$ on Quartz | 300–450 | −0.5–0 | 22.0–24.0 | 2.75–3.35 | 175–225 |
| (2) Twin Wire Arc Spray Al on Stainless Steel | 1100–1450 | 0.30–0.60 | 30.0–32.0 | 2.75–3.25 | 55.0–75.0 |

Table 2 demonstrates that the optimal range of surface profile values that provide desirable characteristics may vary from one type of surface 422 to another. For example, the plasma sprayed aluminum oxide coating may desirably have a negative skewness, whereas the twin wire arc sprayed Al coating may desirably have a positive skewness of, for example, about 0.30 to about 0.60. Thus, by performing a multiparameter analysis on the surface 422 that includes the detection of electrons backscattered from the surface 422, a more complete and thorough characterization of the surface 422 may be provided, and components 410 having the desired surface morphology and characteristics may be selected.

A component 410 thus selected may be a component 410 of a process chamber 100 used for substrate processing, including for example, deposition and etch processing. For example, in one version, the component 410 may be a component of a sputter etching chamber, an embodiment of which is illustrated in FIG. 7a, in which a gas may be energized to sputter etch material from a substrate 110 in the chamber 100 by bombardment of the substrate 110 with ions and neutral particles. As the particles of the gas bombard the substrate 110, the substrate material is sputter etched off the substrate 110 to provide the desired substrate surface. A portion or all of the process chamber 100 may be fabricated from metal or ceramic materials. Metals that may be used to fabricate the process chamber 100 include aluminum, anodized aluminum, "HAYNES 242," "Al-6061," "SS 304," "SS 316," and INCONEL, of which anodized aluminum is sometimes preferred. Suitable ceramic materials include quartz or alumina. For example, in one version, the process chamber 100 comprises an enclosure wall 120 that is fabricated from a ceramic material that is substantially permeable to RF wavelengths, such as quartz. The enclosure wall 120 may serve as a sidewall 130, bottom wall 135, or ceiling 140 of the chamber 100, or may be an internal wall such as a liner or shield 150 positioned adjacent to the sidewalls 130 or ceiling 140. The enclosure wall 120 may be domed shaped to serve as a bell-jar type enclosure that is a separate structure from the sidewall 130 and bottom wall 135 of the chamber 100. The domed enclosure wall 120 may be a cylindrical dome, hemispherical dome, or other single or multiple radius arcuate shaped dome, and is preferably fabricated as a unitary structure.

The process chamber 100 comprises a substrate support 160 to support the substrate 110 in the process chamber 100. The support 160 may comprise an electrode 200 covered by a dielectric layer 170 having a substrate receiving surface 180. An electrode power supply 240 provides a DC or AC bias voltage, for example, an RF bias voltage, to the electrode 200 to energize the gas. Below the electrode 200 is a dielectric plate 190, such as a quartz plate, to electrically isolate the electrode 200 from the other walls 120 of the chamber 100, some of which may be electrically grounded or floating or which may be otherwise electrically biased relative to the electrode 200. The electrically biased electrode 200 allows etching of the substrate 110 by energizing and accelerating the sputter ions toward the substrate 110. At least a portion the wall 120 that is electrically conducting is preferably grounded, so that a negative voltage may be maintained on the substrate 110 with respect to the grounded or floated enclosure wall 120. Optionally, the support 160 may also include an electrostatic chuck (not shown) capable of electrostatically holding the substrate 110 to the support 160, or a DC voltage may be applied to the electrode 200 to generate the electrostatic attractive forces.

The electrode 200 may also comprise one or more conduits (not shown) extending therethrough, such as for example, a gas conduit (not shown) provided to supply heat transfer gas from a heat transfer gas supply (not shown) to the surface 180. The heat transfer gas, typically helium, promotes heat transfer between the substrate 110 and the support 160. Other conduits (not shown) allow lift pins (not shown) to extend through the electrode 200 for loading or unloading of the substrate 110 by a lift mechanism (not shown). The process chamber 100 may also comprise a support lifting mechanism 162 to raise or lower the support 160 in the process chamber 100 to improve, or change the nature of, the processing of the substrate 110.

The wall 120 of the process chamber 100 may also serve as a gas shield 150 to shield parts of the chamber 100 from the energized process gas. For example, the gas shield 150 may substantially shield the lower chamber walls 155 from the process gas. The gas shield 150 also receives and collects the sputtered material from the substrate 110. The gas shield 150 may be suspended within the chamber 100 and include one or more annular rings 390 that may be suspended over the support 160 when the support 160 is retracted downwardly in the process chamber 100. The process chamber 100 may further comprise an electric-magnetic shield 152 to prevent electrical or magnetic fields external to the process chamber 100 from interfering with the operation of the chamber 100. The electric-magnetic shield 152 comprises a material suitable to provide electrical or magnetic shielding, such as a conducting or magnetic alloy.

The process chamber 100 also comprises a gas supply 260 to distribute a process gas into the chamber 100 and a gas exhaust 270 to exhaust the process gas from the chamber 100. In sputter etching, the process gas comprises an inert gas, such as argon or xenon, which does not chemically interact with the substrate material. The gas supply 260 may comprise a process gas supply 280 to supply the process gas and one or more gas conduits 262 to introduce the process gas into the chamber 100 via gas inlets 263, which in one embodiment, are positioned around the periphery of the substrate 110 to introduce the process gas near the substrate 110. For example, the gas supply 260 may comprise about 1 to about 10 gas inlets. Optionally, the gas supply 260 may further comprise a gas trench cover 264 to evenly distribute the flow of the process gas into the chamber 100. The gas trench cover 264 may be coated with a protective coating. The gas inlets 263 are positioned in the gas trench cover 264 to provide uniform dispersion of the process gas in the chamber 100.

The process chamber 100 further comprises one or more mass flow controllers (not shown) to control the flow of the process gas into the chamber 100. The gas exhaust 270 may comprise a pumping channel (not shown) that receives spent process gas, a throttle valve (not shown) to control the pressure of process gas in the chamber 100, and one or more exhaust pumps (not shown). The exhaust pump may comprise, for example, a mechanical pump or a turbo pump, such as a 350 l/s Leybold turbo pump. The gas exhaust 270 may also contain a system for abating undesirable gases from the process gas.

The gas composition and pressure in the chamber 100 is typically achieved by evacuating the chamber 100 down to at least about $10^{-7}$ Torr before back-filling the chamber 100 with argon to a pressure of a few milliTorr. At these gas pressures, the support 160 can be raised upward within the chamber 100. In one embodiment, the process chamber 100 comprises a knob (not shown) that can be rotated by an operator to adjust the height of the substrate 110 in the process chamber 100.

The process chamber 100 further comprises a plasma generator 330 to energize the process gas into a plasma. The plasma generator 330 couples energy to the process gas in a process zone 340 of the process chamber 100 (as shown), or in a remote zone upstream from the process chamber 100 (not shown). In one version, the plasma generator 330 comprises an antenna 350 comprising one or more inductor coils 360. The inductor coils 360 may have a circular symmetry about the center of the process chamber 100. Typically, the antenna 350 comprises one or more solenoids shaped and positioned to provide a strong inductive flux coupling to the process gas. When the antenna 350 is positioned near the ceiling 140 of the process chamber 100, the adjacent portion of the ceiling 140 may be made from a dielectric material, such as silicon dioxide, which is transparent to the electromagnetic radiation emitted by the antenna 350, such as RF power. An antenna power supply 370 provides, for example, RF power to the antenna 350 at a frequency of typically about 50 kHz to about 60 MHz, and more typically about 400 kHz; and at a power level of from about 100 to about 5000 Watts. An RF match network (not shown) may also be provided to match the RF power to an impedance of the process gas. In another version, the plasma generator 330 comprises the electrode 200 to create an electric field in the process zone 340 to energize the process gas. In this version, an electrode power supply (not shown) provides power to the electrode 200, such as at a frequency of from about 50 kHz to about 60 MHz, and more typically about 13.56 MHz. Alternatively or additionally, the plasma generator 330 may comprise a microwave gas activator (not shown).

In yet another version, the component 410 selected according to the present method may be a component 410 of a deposition chamber 100, in which a gas is energized to deposit material, for example by chemical or physical vapor deposition means, on the substrate 110. For example, the component 410 may comprise a component 410 of a chamber 100 in which a gas is energized to sputter material from a target 102 onto the substrate 110. FIG. 7b shows an embodiment of components 410 of a deposition chamber 100 that may be selected according to the present method. In one version, the component 410 may comprise one or more annular rings 390 in the deposition chamber 100 that are about the support 160, such as for example a cover ring 157 and deposition ring 159. The deposition ring 159 and cover ring 157 may cover at least a portion of the support 160 to reduce exposure of the support 160 to energized gas in the chamber 100, and to reduce the deposition of sputtered particles onto the support 160. The deposition ring 159 may at least partially surround the substrate 110 to protect portions of the support 160 not covered by the substrate 110. The cover ring 157 may encircle at least a portion of the deposition ring 159, and help to reduce the deposition of particles onto both the deposition ring 159 and underlying support 160. In another version, the component 410 may comprise a portion of a wall 120 in the chamber 100, such as for example a portion of the gas shield 120. The gas shield 150 may comprise a lower shield 151 that may substantially shield the lower chamber walls 155 from the process gas, and an upper shield 153 that may substantially shield the sidewalls 130 or ceiling 140 from the process gas.

A controller 480 controls operation of the chamber 100 by transmitting and receiving electrical signals to and from the various chamber components and systems. For example, the process conditions measured by the process monitoring system in the process chamber 100 may be transmitted as electrical signals to a controller 480, which then changes process conditions when the signal reaches a threshold value. The controller 480 may be a plurality of controller devices that are connected to one another or a plurality of controller devices that are connected to different components 410 of the process chamber 100.

A process chamber 100 having a component 410 selected according to the present invention, an embodiment of which is shown in FIG. 4c, has significant advantages over a conventional process chamber (not shown) without such selected components 410. For example, components 410 selected by detecting backscattered electrons and generating a signal image may have improved surface properties, such as desired grain sizes and shapes. In one version, the backscattered electrons may be detected to select components 410 comprising surfaces 422 having grains 417 that are sized sufficiently large to allow the sputtered material generated by a sputtering plasma to accumulate on the surface 422 to a desirable thickness substantially without spalling of the textured coating 420 from the underlying structure 437. Thus, by selecting components 410 according to the signal image generated in relation to the backscattered electrons, components 410 may be provided that have enhanced adhesion properties and increased durability in the process environment.

As another example, a process chamber 100 comprising components 410 selected according to their surface properties, such as the size and shape of grains on the surface 422, surface roughness and surface skewness, can reduce redeposition of sputtered material onto the substrate 110 by a factor of five. The bar graph of FIG. 8 shows a normalized number of particles redeposited per substrate 110 as a function of whether the chamber has conventional components (the left bars 830) or components 410 selected according to the present invention (the right bars 835), and also as a function of the redeposition of particle sizes in micrometers. The data points are based on measurements of 11 substrates using two conventional sets of components, and 50 substrates using four sets of components selected according to the present invention. The left and right bars 830, 835 of each bar pair correspond to the amount of redeposition onto a substrate (not shown) in a conventional process chamber with conventional components 410 and a substrate 110 in a process chamber 100 having components 410 selected according to the present invention, respectively. By comparing the left and right bars 830, 835 across the ranges of particle sizes, one can see that the redeposition of material onto the substrate 110 is typically reduced about 5 times with the components 410 selected according to the present method.

Additionally, components 410 selected according to the present method typically have a longer operational lifetime than other conventional components (not shown). In one embodiment, the lifetime of these components is prolonged by at least about 4 times over conventional components, as shown in the bar graph of FIG. 8. A normalized number of redeposited particles of size greater than 0.5 micrometers per operation is plotted, where each bar represents an operation. The bars are arranged chronologically from left to right, and reference number 840 indicates when the components 410 were replaced. The bars on the left side 820 represent operations in a process chamber using conventional components, while bars on the right side 825 represent operations in a process chamber 100 having components 410 according to the present invention. The data points are based on measurements of 11 substrates using chambers with two sets of conventional components, and 50 substrates using chambers with four sets of components 410 selected according to the present invention. The bar 815 is an bad data point that should be disregarded because conventional components used in a corresponding similar operation also provided bad data. The medians of the bar heights on the left and right sides are shown by a horizontal line 805 on the left and another horizontal line 810 on the right. By comparing the median particle redeposition values on the left and right sides 820, 825, respectively, one can see that the particle redeposition amounts are typically reduced by at least about 4 times by using components 410 selected according to the present invention. The component lifetime, which is about proportional to the rate of redeposition of the particles, is thus also typically increased by at least about 4 times.

Although the present invention has been described in considerable detail with regard to certain preferred versions thereof, other versions are possible. For example, the present invention could be used with other process chambers, such as a chemical vapor deposition (CVD) process chamber. The process chamber 100 may also comprise other equivalent configurations as would be apparent to one of ordinary skill in the art. As another example, one or more components 410 of the process chamber 100 may comprise a plurality of different coatings 420. Thus, the appended claims should not be limited to the description of the preferred versions contained herein.

What is claimed is:

1. A method of selecting a component for a substrate processing chamber that processes a substrate in a plasma of an RF or microwave energized gas for deposition or etch processing, the method comprising:
   (a) providing a structure having a textured coating having surface grains; and
   (b) evaluating the resistance of the textured coating on the structure to erosion by the energized gas used in processing the substrate, by:
      (i) directing a beam of electrons onto the surface grains of the textured coating thereby causing at least some of the electrons to be backscattered,
      (ii) detecting the backscattered electrons and generating a signal image,
      (iii) evaluating the signal image to determine the size of the surface grains of the textured coating, and
      (iv) selecting the component when the surface grains of the textured coating are sized from about 0.1 to about 5 micron.

2. A method according to claim 1 wherein (b) (iv) further comprises selecting the component when the surface grains of the textured coating are substantially flower shaped.

3. A method according to claim 1 wherein (b) (iv) comprises selecting the component when the textured coating consists essentially of surface grains sized from about 0.1 to about 5 micron.

4. A method according to claim 1 further comprising evaluating a roughness average and average skewness of the textured coating.

5. A method according to claim 1 wherein (a) comprises forming a structure suitable for a chamber enclosure wall, gas shield, cover ring or deposition ring.

6. A method according to claim 5 comprising forming the structure out of stainless steel, aluminum, titanium, copper, copper alloy, quartz or aluminum oxide.

7. A method according to claim 5 wherein the structure comprises a textured coating comprising aluminum, silicon, aluminum oxide, boron carbide or titanium oxide.

8. A method according to claim 7 wherein the textured coating is a plasma sprayed coating or a thermal sprayed coating.

9. A method according to claim 1 wherein (b) comprises evaluating the resistance of the textured coating to erosion by an energized gas comprising an etching gas that is capable of etching a semiconductor substrate.

10. A method of selecting a component for a substrate processing chamber that processes a substrate in a plasma of an RF or microwave energized gas for deposition or etch processing, the method comprising:
   (a) providing a structure having:
      (i) a shape suitable for a chamber enclosure wall, gas shield, cover ring or deposition ring, the structure being made from stainless steel, aluminum, titanium, copper, copper alloy, quartz or aluminum oxide; and
      (ii) a plasma sprayed coating or a thermal sprayed textured coating on the shape, the textured coating having surface grains comprising one or more of aluminum, silicon, aluminum oxide, boron carbide and titanium oxide; and
   (b) evaluating the resistance of the textured coating to erosion by the energized gas used in processing the substrate by:
      (i) directing a beam of electrons onto the surface grains of the textured coating thereby causing at least some of the electrons to be backscattered,
      (ii) detecting the backscattered electrons and generating a signal image,
      (iii) evaluating the signal image to determine the size of the surface grains of the textured coating, and
      (iv) selecting the component when the surface grains of the textured coating are sized from about 0.1 to about 5 micron and are substantially flower shaped.

11. A method of selecting a component for a substrate processing chamber that is used to process a substrate in a plasma of an RF or microwave energized gas for deposition or etch processing, the method comprising:
   (a) providing a structure having a textured coating with surface grains and a surface topography; and
   (b) evaluating the resistance of the textured coating on the structure to erosion by the RF energized gas that is used to process the substrate, by:

(i) directing a beam of electrons onto the surface grains of the textured coating thereby causing at least some of the electrons to be backscattered,
(ii) detecting the backscattered electrons and generating a signal image comprising variations in image contrast,
(iii) evaluating the variations in image contrast of the signal image to determine the surface topography and size of surface grains of the textured coating, and
(iv) selecting the component when the surface grains of the textured coating are sized from about 0.1 to about 5 micron and the surface topography comprises substantially flower shaped surface grains.

12. A method according to claim 11 wherein (b) (iv) comprises selecting the component when the textured coating consists essentially of surface grains sized from about 0.1 to about 5 micron.

13. A method according to claim 11 further comprising evaluating a roughness average of the surface of the textured coating and selecting the component when the roughness average is from about 150 microinches to about 450 microinches.

14. A method according to claim 11 further comprising evaluating a skewness of the surface of the textured coating and selecting the component when the skewness is from about −0.7 to about 0.1.

15. A method according to claim 11 wherein (a) comprises forming a structure comprising a chamber enclosure wall, gas shield, cover ring or deposition ring.

16. A method according to claim 15 comprising forming the structure out of stainless steel, aluminum, titanium, copper, copper alloy, quartz or aluminum oxide.

17. A method according to claim 15 wherein the structure comprises a textured coating comprising aluminum, silicon, aluminum oxide, boron carbide or titanium oxide.

* * * * *